US00PP30097P3

(12) United States Plant Patent
Qiangmin et al.

(10) Patent No.: US PP30,097 P3
(45) Date of Patent: Jan. 15, 2019

(54) ***CAMELLIA* PLANT NAMED 'HB051'**

(50) Latin Name: ***Camellia* hybrid**
Varietal Denomination: HB051

(71) Applicants: Zhao Qiangmin, Guangzhou (CN); Gao Jiyin, Guangzhou (CN); Liu Xinkai, Guangzhou (CN)

(72) Inventors: Zhao Qiangmin, Guangzhou (CN); Gao Jiyin, Guangzhou (CN); Liu Xinkai, Guangzhou (CN)

(73) Assignee: Palm Eco-Town Development Co., Ltd., Guangzhou (CN)

( * ) Notice: Subject to any disclaimer, the term of this patent is extended or adjusted under 35 U.S.C. 154(b) by 0 days.

(21) Appl. No.: 15/732,758

(22) Filed: Dec. 23, 2017

(65) Prior Publication Data

US 2018/0192564 P1 Jul. 5, 2018

Related U.S. Application Data

(60) Provisional application No. 62/498,661, filed on Dec. 31, 2016.

(51) Int. Cl.
*A01H 5/02* (2018.01)
*A01H 5/12* (2018.01)

(52) U.S. Cl.
USPC ..... Plt./244
CPC ..... *A01H 5/02* (2013.01); *A01H 5/12* (2013.01)

(58) Field of Classification Search
USPC ..... Plt./244
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Camellia* plant named 'HB051', characterized by its sturdy upright to outwardly branching plant habit; vigorous growth habit and rapid growth rate; freely branching habit, dense and bushy appearance; large leathery dark green-colored leaves; long flowering period; light red purple-colored semi-double to peony-type form flowers; and good garden performance including tolerance to full sunlight conditions.

2 Drawing Sheets

Botanical designation: *Camellia* hybrid.
Cultivar denomination: 'HB051'.

BACKGROUND OF THE INVENTION

The present Invention relates to a new and distinct cultivar of *Camellia* plant, botanically known as *Camellia* hybrid, and hereinafter referred to by the name 'HB051'.

The new *Camellia* plant is a product of a planned breeding program conducted by the Inventors in Zhaoqing, China. The objective of the breeding program is to create new fast-growing *Camellia* plants that flower year-round and tolerate full sunlight.

The new *Camellia* plant originated from a cross-pollination conducted by the Inventors in February, 2007 in Zhaoqing, China of an unnamed seedling selection of *Camellia amplexicaulis*, not patented, as the female, or seed, parent with *Camellia* hybrid 'Scented Swirl', not patented, as the male, or pollen, parent. The new *Camellia* plant was discovered and selected by the Inventors as a single plant from within the progeny of the stated cross-pollination in a controlled environment in Zhaoqing, China in November, 2010.

Asexual reproduction of the new *Camellia* plant by grafting cuttings onto an unnamed selection of *Camellia gaozhouensis*, not patented, in a controlled greenhouse environment in Zhaoqing, China has shown that the unique features of this new *Camellia* plant are stable and reproduced true to type in successive generations.

SUMMARY OF THE INVENTION

Plants of the new *Camellia* have not been observed under all possible combinations of environmental conditions and cultural practices. The phenotype may vary somewhat with variations in environment such as temperature and light intensity without, however, any variance in genotype.

The following traits have been repeatedly observed and are determined to be the unique characteristics of 'HB051'. These characteristics in combination distinguish 'HB051' as a new and distinct cultivar of *Camellia:*

1. Sturdy upright to somewhat outwardly branching plant habit.
2. Vigorous growth habit and rapid growth rate.
3. Freely branching habit, dense and bushy appearance.
4. Large leathery dark green-colored leaves.
5. Long flowering period.
6. Light red purple-colored semi-double to peony-type form flowers.
7. Good garden performance, tolerant to full sunlight conditions.

Plants of the new *Camellia* differ from plants of the female parent selection primarily in the following characteristics:

1. Leaves of plants of the new *Camellia* are slightly smaller than and not as glossy as leaves of plants of the female parent selection.
2. Flowers of plants of the new *Camellia* are semi-double to peony-type in form whereas flowers of the female parent selection are single in form.

Plants of the new *Camellia* differ primarily from plants of the male parent, 'Scented Swirl', in the following characteristics:

1. Leaves of plants of the new *Camellia* are larger than leaves of plants of 'Scented Swirl'.

2. Flowers of plants of the new *Camellia* are semi-double to peony-type in form whereas flowers of 'Scented Swirl' are single in form.
3. Plants of the new *Camellia* flower for a longer period of time than plants of 'Scented Swirl'.

Plants of the new *Camellia* can be compared to the plants of *Camellia* hybrid 'Golden Purple Crown', not patented. In side-by-side comparisons plants of the new *Camellia* differ from plants of the 'Golden Purple Crown' in the following characteristics:

1. Leaves of plants of the new *Camellia* are larger than leaves of plants of 'Golden Purple Crown'.
2. Flowers of plants of the new *Camellia* are semi-double to peony-type in form whereas flowers of 'Golden Purple Crown' are peony-type in form.
3. Plants of the new *Camellia* flower for a longer period of time than plants of 'Golden Purple Crown'.

Plants of the new *Camellia* can be compared to the plants of *Camellia japonica* 'Covina', not patented. In side-by-side comparisons plants of the new *Camellia* differ from plants of the 'Covina' in the following characteristics:

1. Leaves of plants of the new *Camellia* are larger than leaves of plants of 'Covina'.
2. Flowers of plants of the new *Camellia* are semi-double to peony-type in form whereas flowers of 'Covina' are semi-double to rose-double in form.
3. Plants of the new *Camellia* flower for a longer period of time than plants of 'Covina'.

BRIEF DESCRIPTION OF THE PHOTOGRAPHS

The accompanying colored photographs illustrate the overall appearance of the new *Camellia* plant showing the colors as true as it is reasonably possible to obtain in colored reproductions of this type. Colors in the photographs may differ slightly from the color values cited in the detailed botanical description, which accurately describe the colors of the new *Camellia* plant.

The photograph on the first sheet is a side perspective view of a typical flowering plant of 'HB051' grown in an outdoor nursery.

The photograph on the second sheet are close-up views of the upper and lower surfaces of a typical leaf, a typical terminal vegetative branch, a typical terminal branch with developing flower buds, a typical developing flower bud and a typical terminal branch with a fully open flower of 'HB051'.

DETAILED BOTANICAL DESCRIPTION

The aforementioned photographs and following observations and measurements describe plants grown in Zhaoqing, China in ground beds in an outdoor nursery during the autumn and under cultural practices typical of commercial *Camellia* production. During the production of the plants, day temperatures ranged from 18° C. to 33° C. and night temperatures ranged from 11° C. to 26° C. Plants were six years old when the photographs and description were taken. In the following description, color references are made to The Royal Horticultural Society Colour Chart, 2007 Edition, except where general terms of ordinary dictionary significance are used.

Botanical classification: *Camellia* hybrid 'HB051'.

Parentage:

*Female, or seed, parent*.—Unnamed seedling selection of *Camellia amplexicaulis*, not patented.

*Male, or pollen, parent*.—*Camellia* hybrid 'Scented Swirl', not patented.

Propagation:

*Type*.—By grafting cuttings onto a rootstock, an unnamed selection of *Camellia gaozhouensis*, not patented.

*Time to produce a rooted young plant, summer*.—About three months at temperatures about 28° C.

*Time to produce a rooted young plant, winter*.—About four months at temperatures about 8° C.

Plant description:

*Plant form and growth habit*.—Perennial evergreen shrub; sturdy upright plant habit; vigorous growth habit; rapid growth rate.

*Branching habit*.—Freely branching habit; about two primary lateral branches each with about two to three secondary branches; dense and bushy appearance.

*Plant height*.—About 213 cm.

*Plant diameter, area of spread*.—About 151 cm.

*Lateral branch description*.—Length: About 112 cm. Diameter: About 1.2 cm. Internode length: About 2.1 cm. Strength: Strong. Aspect: Upright to about 25° to 35° from vertical. Texture and luster: Smooth, glabrous; glossy; woody with development. Color, young stems: Close to 144A. Color, older stems: Close to N199C.

*Leaf description*.—Arrangement: Alternate, single. Length: Large, about 10.1 cm. Width: About 3.9 cm. Shape: Oblong. Apex: Cuspidate. Base: Obtuse. Margin: Serrate. Venation pattern: Pinnate, arcuate. Texture and luster, upper surface: Smooth, glabrous; leathery; moderately glossy. Texture and luster, lower surface: Smooth, glabrous; leathery; matte. Color: Developing leaves, upper and lower surfaces: Close to 179C. Fully expanded leaves, upper surface: Close to 139A; venation, close to 144A; color does not change during the autumn. Fully expanded leaves, lower surface: Close to 146B; venation, close to N144A; color does not change during the autumn.

*Petioles*.—Length: About 5 mm. Diameter: About 3 mm. Texture and luster, upper and lower surfaces: Smooth, glabrous; leathery; matte. Color, upper and lower surfaces: Close to 144A.

Flower description:

*Flower arrangement and appearance*.—Semi-double to peony-type rotate flowers, flowers terminal and axillary; freely flowering habit with usually about 874 flowers and flower buds developing per plant; flowers face mostly outwardly.

*Natural flowering season*.—Plants of the new *Camellia* flower year-round in Zhaoqing, China.

*Postproduction longevity*.—Plants maintain good flower substance for about three to four days on the plant; flowers persistent.

*Fragrance*.—None detected.

*Flower diameter*.—About 10.3 cm.

*Flower depth*.—About 5.2 cm.

*Flower buds*.—Length: About 3 cm. Diameter: About 1.8 cm. Shape: Ovoid. Texture and luster: Smooth, glabrous; leathery; matte. Color: Close to 146A.

*Petals and petaloids*.—Quantity and arrangement: About 28 to 30 imbricate petals and petaloids arranged in numerous whorls. Length: About 4.5 cm to 4.8 cm. Width: About 2.4 cm to 2.6 cm. Shape: Obovate. Apex: Retuse. Base: Cuneate. Margin:

Entire; slightly to moderately undulate. Texture and luster, upper and lower surfaces: Smooth, glabrous; silky; matte. Color: When opening and fully opened, upper surface: Close to between 65B and 68A; venation, close to between 65C and 68B; color becoming closer to 68A with development. When opening and fully opened, lower surface: Close to between 65B and 68A; venation, close to between 65C and 68B; color becoming closer to 68A with development.

*Sepals*.—Quantity and arrangement: About four imbricate sepals arranged in an ovate-shaped calyx. Length: About 9 mm. Width: About 1.6 cm. Shape: Ovate. Apex: Obtuse. Base: Truncate. Margin: Entire. Texture and luster, upper and lower surfaces: Smooth, glabrous; leathery; matte. Color: When opening and fully opened, upper surface: Close to 137A. When opening and fully opened, lower surface: Close to N144A.

*Peduncles*.—Length: About 1 cm. Diameter: About 4 mm. Aspect: About 20° to 30° from stem axis. Strength: Strong. Texture and luster: Smooth, glabrous; matte. Color: Close to N137C.

*Reproductive organs*.—Androecium: Quantity per flower: About 84. Filament length: About 2.6 cm. Filament color: Close to 49B. Anther shape: Narrowly oblong. Anther size: About 1 mm by 1.4 mm. Anther color: Close to 8A. Pollen amount: Moderate. Pollen color: Close to 8A. Gynoecium: Quantity of pistils per flower: About five to six. Pistil length: About 2.2 cm. Style length: About 1.8 cm. Style color: Close to 2D. Stigma diameter: About 3 mm. Stigma color: Close to 2D. Ovary color: Close to 10A.

*Fruits and seeds*.—Fruit and seed production have not been observed on plants of the new *Camellia* to date.

Garden performance: Plants of the new *Camellia* have been observed have good garden performance and to tolerate rain, wind, full sunlight and temperatures ranging from about 3° C. to about 32° C.

Pathogen & pest resistance: Plants of the new *Camellia* have not been observed to be resistant to pathogens and pests common to *Camellia* plants to date.

It is claimed:

1. A new and distinct cultivar of *Camellia* plant named 'HB051' as illustrated and described.

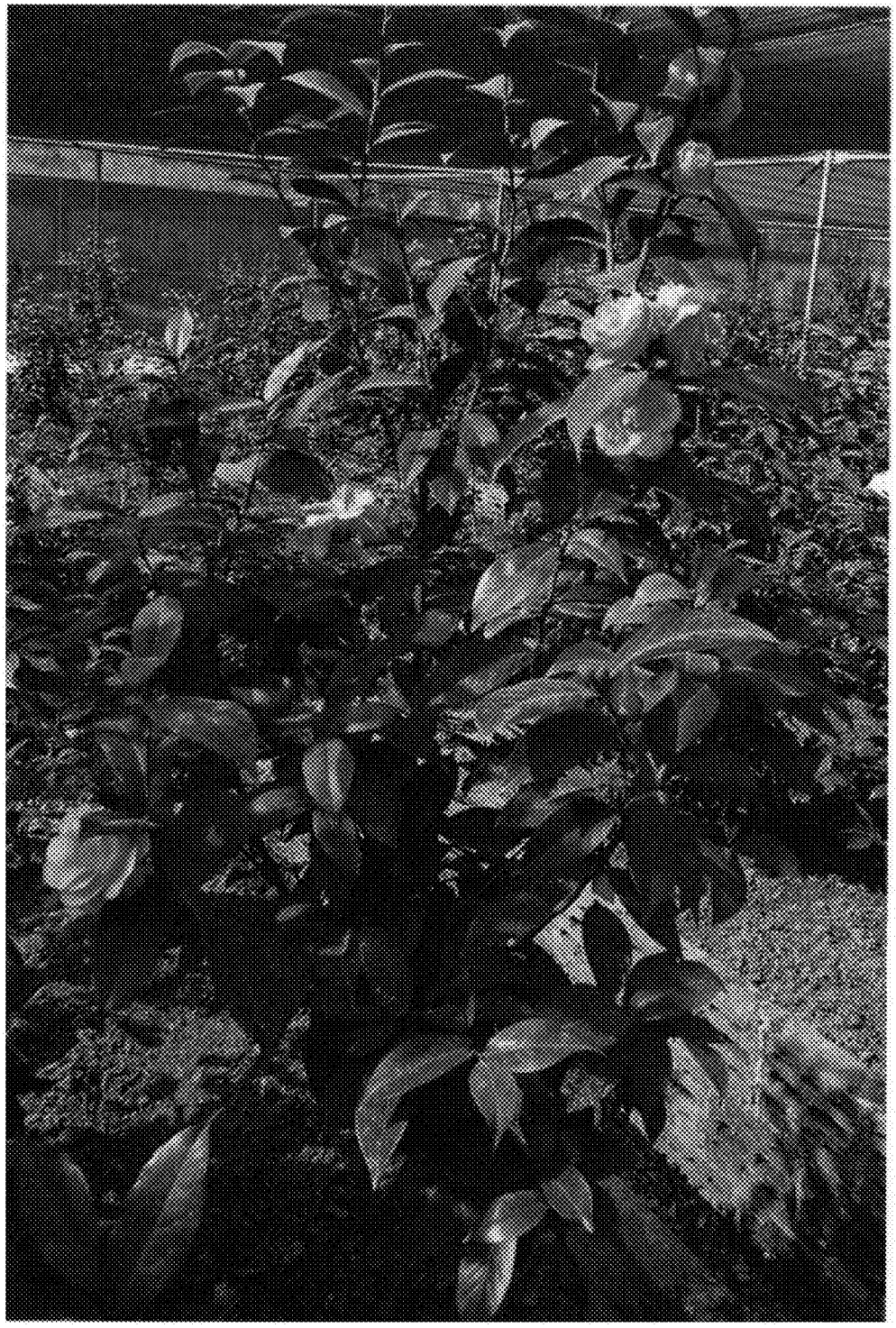

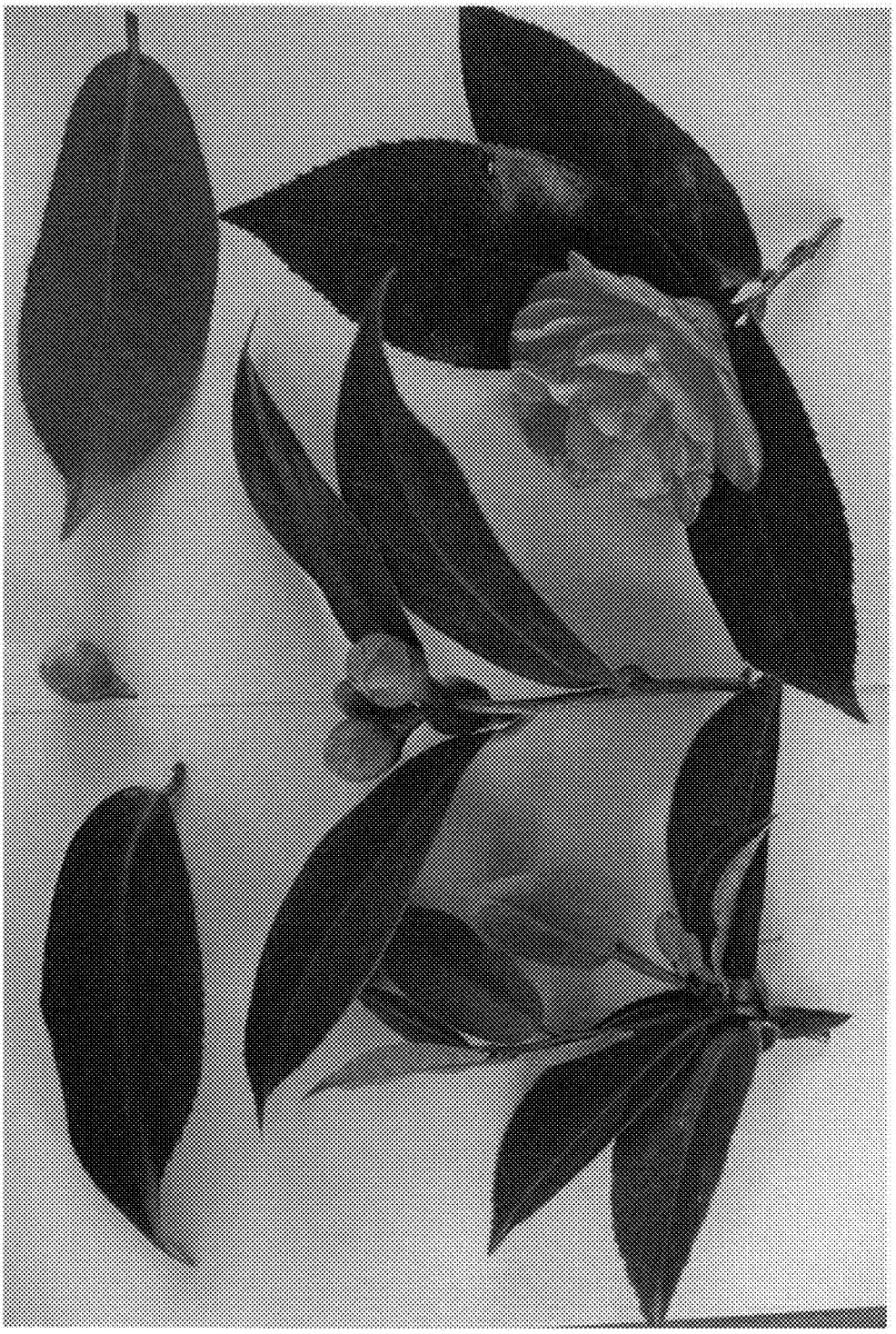

* * * * *